US012761227B2

(12) United States Patent
Li et al.

(10) Patent No.: US 12,761,227 B2
(45) Date of Patent: Oct. 13, 2026

(54) COMPOSITIONS AND METHODS FOR DIAGNOSING AND/OR TREATING CHRONIC KIDNEY DISEASE

(71) Applicant: Société des Produits Nestlé S.A., Vevey (CH)

(72) Inventors: Qinghong Li, Chesterfield, MO (US); Loïc Dayon, Colombier (CH); Ornella Cominetti Allende, Denges (CH); Charlotte Macron, Lausanne (CH)

(73) Assignee: Société des Produits Nestlé S.A., Vevey (CH)

( * ) Notice: Subject to any disclaimer, the term of this patent is extended or adjusted under 35 U.S.C. 154(b) by 225 days.

(21) Appl. No.: 18/775,840

(22) Filed: Jul. 17, 2024

(65) Prior Publication Data

US 2025/0035648 A1 Jan. 30, 2025

Related U.S. Application Data

(60) Provisional application No. 63/516,211, filed on Jul. 28, 2023.

(51) Int. Cl.

*G01N 33/68* (2006.01)
*A61K 31/198* (2006.01)
*A61K 31/202* (2006.01)
*A61K 31/355* (2006.01)
*A61K 45/06* (2006.01)

(52) U.S. Cl.

CPC ....... *G01N 33/6893* (2013.01); *A61K 31/198* (2013.01); *A61K 31/202* (2013.01); *A61K 31/355* (2013.01); *A61K 45/06* (2013.01); *G01N 33/6857* (2013.01); *G01N 2333/78* (2013.01); *G01N 2333/914* (2013.01); *G01N 2333/96444* (2013.01); *G01N 2800/347* (2013.01)

(58) Field of Classification Search

None

See application file for complete search history.

(56) References Cited

U.S. PATENT DOCUMENTS

| | | | | |
|---|---|---|---|---|
| 2009/0258830 A1* | 10/2009 | Thadhani | A61P 13/12 | 514/6.5 |
| 2010/0056445 A1 | 3/2010 | Sharma et al. | | |
| 2012/0135428 A1 | 5/2012 | Kronenberg | | |
| 2013/0344196 A1* | 12/2013 | Al-Murrani | A23K 50/40 | 435/6.12 |
| 2015/0247872 A1* | 9/2015 | Thadhani | A61K 31/59 | 435/7.92 |
| 2021/0268110 A1* | 9/2021 | Ma | A61K 47/14 | |

FOREIGN PATENT DOCUMENTS

WO 2023126759 A1 7/2023

OTHER PUBLICATIONS

Choi et al., "Serum Concentrations of Leptin and Adiponectin in Dogs with Chronic Kidney Disease", Journal of Veterinary Internal Medicine, vol. 36, Issue No. 4, May 27, 2022, pp. 1330-1340, XP093201451.

Kongtasai et al., "Renal Biomarkers in Cats: A Review of the Current Status in Chronic Kidney Disease", Journal of Veterinary Internal Medicine, vol. 36, Issue No. 2, Feb. 26, 2022, pp. 379-396, XP093024432.

Przybycinski et al., "Adiponectin in Chronic Kidney Disease", International Journal of Molecular Sciences, vol. 21, Issue No. 24, Dec. 9, 2020, pp. 1-17, XP093201432.

Kawano et al., "Molecular Composition of Adiponectin in Urine is a Useful Biomarker for Detecting Early Stage of Diabetic Kidney Disease", The Journal of Medical Investigation, vol. 70, Jan. 1, 2023, pp. 464-470, XP093201436.

Pérez-López et al., "Animal Models and Renal Biomarkers of Diabetic Nephropathy", Advances in Experimental Medicine and Biology, vol. 1307, Jan. 1, 2021, pp. 521-551, XP093201449.

International Search Report and Written Opinion to PCT application No. PCT/IB2024/056944 dated Oct. 10, 2024.

International Renal Interest Society (IRIS) guidelines (modified 2019) (http://www.iris-kidney.com/guidelines/staging.html). Aug. 3, 2023.

Ford et al. "Precision of a Clinical Metabolomics Profiling Platform for Use in the Identification of Inborn Errors of Metabolism" Appl Lab Med 2020, pp. 342-356.

Li et al. "Metabolomics Analysis Reveals Deranged Energy Metabolism and Amino Acid Metabolic Reprogramming in Dogs With Myxomatous Mitral Valve Disease" J Am Heart Assoc 2021. pp. 1-14.

Dayon et al L "A highly automated shotgun proteomic workflow: Clinical scale and robustness for biomarker discovery in blood" Methods in Molecular Biology. 2017;1619:433-449.

Mctaggart et al "The diagnostic accuracy of a urine albumin-creatinine ratio point-of-care test for detection of albuminuria in primary care" Am J Kidney Dis. 2012;60:787-794.

(Continued)

*Primary Examiner* — Blaine Lankford

(57) ABSTRACT

Compositions and methods diagnose and/or treat chronic kidney disease (CKD) using one or more feline circulating proteins as markers for early-stage CKD. A method of diagnosing chronic kidney disease (CKD) in a feline can include measuring an amount of each of at least one circulating protein from the feline. The at least one circulating protein is one or more of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof. The method also includes performing comparison of the amount of each of the at least one circulating protein from the feline to a corresponding predetermined value or a corresponding predetermined range. The method also includes diagnosing the feline as having early-stage CKD or not having early-stage CKD, based on the comparison.

20 Claims, No Drawings

(56) References Cited

OTHER PUBLICATIONS

Hoste et al "Routine serum creatinine measurements: How well do we perform?" BMC Nephrol. 2015;16:21.

Baral et al "Comparison of serum and plasma sdma measured with point-of-care and reference laboratory analysers: Implications for interpretation of sdma in cats" J Feline Med Surg. 2021;23:906-920.

Dayon "Comprehensive and scalable highly automated ms-based proteomic workflow for clinical biomarker discovery in human plasma" J. Proteome Res. 2014;13:3837-3845.

Perkins et al "Probability-based protein identification by searching sequence databases using mass spectrometry data" Electrophoresis. 1999;20:3551-3567.

Chambers et al "A cross-platform toolkit for mass spectrometry and proteomics" Nat. Biotechnol. 2012;30:918-920.

Yamakado et al "Urinary adiponectin as a new diagnostic index for chronic kidney disease due to diabetic nephropathy" BMJ Open Diabetes Res Care. 2019;7:e000661.

Vanhoek et al "Immunoassay of urinary retinol binding protein as a putative renal marker in cats" J Immunol Methods. 2008;329:208-213.

Sawashima et al "Expression of alpha-smooth muscle actin and fibronectin in tubulointerstitial lesions of cats with chronic renal failure" Am J Vet Res. 2000;61:1080-1086.

* cited by examiner

COMPOSITIONS AND METHODS FOR DIAGNOSING AND/OR TREATING CHRONIC KIDNEY DISEASE

CROSS REFERENCE TO RELATED APPLICATIONS

This application claims the benefit of and priority to U.S. Provisional Application Ser. No. 63/516,211 filed Jul. 28, 2023, the disclosure of which is incorporated in its entirety herein by this reference.

TECHNICAL FIELD

The present disclosure relates generally to renal health in an animal such as a companion animal. In some embodiments, compositions and methods diagnose and/or treat early-stage chronic kidney disease (CKD) in a feline using one or more circulating proteins as biomarkers for the early-stage CKD.

BACKGROUND

The kidneys have five primary functions. They filter waste products from the body (e.g., urea and creatinine), regulate electrolytes (e.g., potassium, calcium, phosphorus, and sodium), produce erythropoietin (which stimulates bone marrow to produce red blood cells), produce rennin (which controls blood pressure), and produce and concentrate urine.

Chronic kidney disease ("CKD") is a progressive kidney disease which has four phases: loss of renal reserve, renal insufficiency, azotemia, and uremia. The kidneys have a large built-in reserve because only approximately 30% of kidney capacity is needed for normal kidney function. Kidney capacity diminishes with time for a variety of reasons, for example, advanced age, diseases, and medications that damage the kidney(s). Renal insufficiency is characterized by decrease in renal function and is generally observed when about 70% of kidney function has been lost (i.e., when only about 30% of kidney capacity is available). Clinical signs are typically not obvious during the stages of loss of renal reserve and renal insufficiency, thereby making it difficult to detect CKD.

Stage 1 CKD is non-azotemic and generally can be difficult for diagnosis because there are no overt clinical symptoms. Stage 2 CKD is mildly azotemic with clinical signs absent or mild. Stages 1 and 2 can be generally grouped together as "early-stage CKD." Then Stage 3 is moderately azotemic with clinical signs present, and Stage 4 is severely azotemic with clinical signs present.

CKD is a terminal disease and is one of the leading causes of death in felines. Currently, diagnosis of chronic kidney disease (CKD) in cats is based on progressive changes in parameters in blood chemistry and urinalysis, including blood creatinine, symmetric dimethylarginine (SDMA), urine specific gravity and urine protein and creatine ratio.

SUMMARY

Applicant recognized that the sensitivity and specificity for detecting CKD is limited under current methods. First, current methods measure serum creatinine concentration using enzymatic reactions that can be detected using the spectrophotometric assay, but large inter-assay differences still exist, and the inaccuracy in the lower concentration range is of particular concern. Second, bias and imprecision were also reported in SDMA assays. Third, glomerular filtration rate is currently the gold standard for measuring renal impairment, but its current measurement techniques are long and not feasible for routine veterinary practice and screening.

Detection of Stage 1 CKD is especially challenging because blood creatinine and SDMA are rising within the reference interval. Multiple blood samplings and evaluations at different times are necessary to diagnose Stage 1 CKD for certainty. The multiple blood samplings and evaluations are one of the main reasons that cats having early-stage CKD often are undiagnosed until the disease progresses into a more advanced stage, missing the window of opportunity for early diagnosis and intervention.

Applicant identified seven feline circulating proteins as markers for early-stage CKD in cats, specifically, adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), and fibronectin (FN1). These seven serum proteins can be used alone or in combination as diagnostic markers in cats with early-stage CKD.

Accordingly, the present disclosure relates generally to compositions and methods for diagnosis and/or treatment of CKD in a feline. In a preferred embodiment, a method of diagnosing early-stage CKD in a feline can comprise measuring an amount of each of at least one circulating protein selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof. In some embodiments, the method can measure at least two of these circulating proteins, for example at least three, at least four, at least five, at least six, or even all seven of these circulating proteins, as biomarkers for early-stage CKD. In some embodiments, the early-stage CKD is Stage 1 CKD. In some embodiments, the method comprises obtaining a sample of at least one of serum or plasma from the feline, and the measuring of the amount of each of the at least one circulating protein is performed on the sample of at least one of serum or plasma from the feline.

The method can further comprise comparison of the amount of each of the at least one circulating protein measured in the feline (e.g., measured in plasma and/or serum obtained from the feline) to a corresponding predetermined value or corresponding predetermined range (e.g. as shown in Table 2). The method can further comprise diagnosing the feline as having early-stage CKD or not having early-stage CKD, based on the comparison of the amount of each of the at least one circulating protein measured from the feline to the corresponding predetermined value or corresponding predetermined range.

In another embodiment, a method of treating or slowing progression of CKD in a feline comprises any of the methods of diagnosing early-stage CKD in the feline as disclosed herein. The method of treating or slowing progression of CKD further comprises recommending a composition for the feline, providing a composition for the feline, and/or administering a composition to the feline, wherein the composition treats or slows the progression of CKD in the feline. For example, the composition can be administered to the feline in an amount effective to treat or slow the progression of CKD.

Advantageously, a biomarker as disclosed herein is indicative of a disease state (or health status) and can be measured accurately and reproducibly. In addition, during pharmaceutical or nutritional interventions, a biomarker can also be an indicator for treatment efficacy. Protein-based markers can demonstrate how pets react to a therapy. Monitoring the changes in protein biomarkers in peripheral blood can be a very powerful tool for diagnosis and staging, but also be used to document the outcome of an intervention in cats with CKD. Blood sampling can be easily repeated and presents limited invasiveness.

An advantage of one or more embodiments of the compositions and methods disclosed herein is diagnosis and/or prevention of CKD in felines, for example by diagnosis and/or treatment of early-stage CKD.

Another advantage of one or more embodiments of the compositions and methods disclosed herein is treatment of CKD which provides partial or complete relief.

Yet another advantage of one or more embodiments of the compositions and methods disclosed herein is more accurate diagnosis of CKD.

Still another advantage of one or more embodiments of the compositions and methods disclosed herein is novel protein biomarkers that may provide improved sensitivity and practical clinical utility, for example their combination using mathematical modelling, and that can be measured using a variety of technologies, including immuno-assays and mass spectrometry-based assays.

And another advantage of one or more embodiments of the compositions and methods disclosed herein is personalized diet recommendations based on diagnosis of early-stage CKD in a feline.

Another advantage of one or more embodiments of the compositions and methods disclosed herein is particular pet food products based on diagnosis of early-stage CKD in a feline.

Additional features and advantages are described herein and will be apparent from the following Detailed Description.

DETAILED DESCRIPTION

Definitions

As used in this disclosure and the appended claims, the singular forms “a,” “an” and “the” include plural referents unless the context clearly dictates otherwise. Thus, for example, reference to “a composition” or “the composition” includes two or more compositions. The terms “and/or” and “at least one of” used in the respective context of “X and/or Y” and “at least one of” should be interpreted as “X,” or “Y,” or “X and Y.” Where used herein, the terms “example” and “such as,” particularly when followed by a listing of terms, are merely exemplary and illustrative, and are not exclusive or comprehensive.

As used herein, “about” is understood to refer to numbers in a range of numerals, for example the range of −10% to +10% of the referenced number, within-5% to +5% of the referenced number, or in one aspect, within-1% to +1% of the referenced number, and in a specific aspect, within-0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the composition on a dry matter basis unless specifically stated otherwise. The skilled artisan will appreciate that the term “dry matter basis” means that an ingredient’s concentration or percentage in a composition is measured or determined after any free moisture in the composition has been removed. When reference is made to the pH, values correspond to pH measured at 25° C. with standard equipment. An “amount” can be the total amount of the referenced component per serving of the composition or per distinct unit of the composition and/or can be the weight percentage of the referenced component by dry weight. Moreover, an “amount” includes zero; for example, the recitation of an amount of a compound does not necessarily mean that the compound is present, unless followed by a range that excludes zero.

The terms “food,” “food product” and “food composition” mean a product or composition that is intended for ingestion by an animal and provides at least one nutrient to the animal. Further in this regard, these terms mean that the product or composition is in a form ready for consumption and is not merely an intermediate from which a consumable product or composition is made, although other food compositions can be added in some embodiments. The term “pet food” means any food composition intended to be consumed by a pet. The term “pet” means any animal which could benefit from or enjoy the compositions provided by the present disclosure. For example, the pet can be an avian, bovine, canine, equine, feline, hircine, lupine, murine, ovine, or porcine animal, but the pet can be any suitable animal.

The term “complete and balanced” when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO) as of Jan. 1, 2023.

The term “companion animal” means a dog or a cat. In an embodiment, the compositions and methods disclosed herein involve a senior cat. As used herein, a “senior cat” has an age of at least 7 years, and in some embodiments, has an age of at least 10 years.

As used herein, a “circulating protein” is a protein located in and/or isolated from at least one of serum or plasma. Some embodiments of the methods disclosed herein comprise obtaining a sample of at least one of serum or plasma from the animal (e.g., feline) and measuring the amount of the circulating protein in the sample of at least one of serum or plasma.

As used herein, “chronic kidney disease” or “CKD” is defined as the presence of structural or functional abnormalities of one or both kidneys that have been present for 3 months or longer. In one embodiment, the CKD can be diagnosed as one of 4 stages as defined by the International Renal Interest Society (IRIS) guidelines (modified 2019) (http://www.iris-kidney.com/guidelines/staging.html).

As used herein, “early-stage chronic kidney disease” or “early-stage CKD” refers to Stage 1 and/or Stage 2 of chronic kidney disease.

As used herein, “late-stage chronic kidney disease” or “late-stage CKD” refers to Stage 3 and/or Stage 4 of chronic kidney disease.

The term “B vitamin” refers to any B vitamin including derivatives, acidic forms, and salts thereof. Such B vitamins can include, without limitation, vitamin B1 (thiamine), vitamin B2 (riboflavin), vitamin B3 (niacin, nicotinic acid, nicotinamide), vitamin B5 (pantothenic acid), vitamin B6 (pyridoxine, pyridoxal, pyridoxamine), vitamin B7 (biotin), vitamin B8 (myo-inositol), vitamin B9 (folic acid), vitamin B12 (cobalamin compounds including methylcobalamin, hydroxocobalamin, and cyanocobalamin).

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "effective amount" of "therapeutically effect amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some aspects, the particular disease, condition, or disorder can be chronic kidney disease.

The term "dietary supplement" means a product that is intended to be ingested in addition to the normal animal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging animals, the animal will continue consuming on a regular basis for the remainder of its life. This can also be referred to as consumption for "extended" periods.

The term "regular basis" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, are relevant prior art for the present invention and the right to challenge the accuracy and pertinence of such patents, patent applications, publications, and other references is specifically reserved.

EMBODIMENTS

In a preferred embodiment, a method of diagnosing early-stage chronic kidney disease (CKD) in a feline can comprise measuring an amount of each of at least one circulating protein selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof. In some embodiments, the method can measure at least two of these circulating proteins, for example at least three, at least four, at least five, at least six, or even all seven of these circulating proteins, as biomarkers for early-stage CKD.

The feline may be a senior cat. In some embodiments, the early-stage CKD is Stage 1 CKD. Optionally, the method comprises obtaining a sample of at least one of serum or plasma from the feline, and the measuring of the amount of the at least one circulating protein is performed on the sample. In some embodiments, the amount is a normalized relative abundance or absolute quantification of the at least one circulating protein, for example a normalized relative abundance or absolute quantification of the at least one circulating protein in a sample of at least one of serum or plasma from the feline. As used herein, "normalized relative abundance" refers to the area-under-the-curve of ion counts of each biomarker, as measured by liquid chromatography and mass spectrometry, further transformed using logarithm base 2 and auto-scaled to achieve a zero mean and unit variance. Such measurements are known in the art and have been described by Metabolon Inc. For example, details and further information are found in Ford et al. Appl Lab Med 2020 and Li et al. J Am Heart Assoc 2021.

The method can further comprise comparison of the amount of each of the at least one circulating protein measured from the feline (e.g., measured in plasma and/or serum obtained from the feline) to a corresponding predetermined value or a corresponding predetermined range. The method can further comprise diagnosing the feline as having early-stage CKD or not having early-stage CKD, based on the comparison.

In some preferred embodiments, the predetermined value is a mean amount of the circulating protein in felines that do not have any CKD, and/or the predetermined range is a range comprising a mean amount of the circulating protein in felines that do not have any CKD. Preferably such a range comprises (i) a set of predetermined values less than the mean amount of the circulating protein in felines that do not have any CKD, (ii) the mean amount of the circulating protein in felines that do not have any CKD, and (iii) a set of predetermined values greater than the mean amount of the circulating protein in felines that do not have any CKD.

For example, some embodiments of the method diagnose the feline as having early-stage CKD if the feline's measured amount of ADIPOQ exceeds a predetermined value, such as a mean amount of ADIPOQ in felines that do not have any CKD, or is outside of a predetermined range, such as a range comprising a mean amount of ADIPOQ in felines that do not have any CKD.

Additionally or alternatively, some embodiments of the method diagnose the feline as not having early-stage CKD if the feline's measured amount of ADIPOQ is equal to or less than a predetermined value, such as a mean amount of ADIPOQ in felines that do not have any CKD, or is within a predetermined range, such as a range comprising a mean amount of ADIPOQ in felines that do not have any CKD.

Additionally or alternatively, some embodiments of the method diagnose the feline as having early-stage CKD if the feline's measured amount of CAMP exceeds a predetermined value, such as a mean amount of CAMP in felines that do not have any CKD, or is outside of a predetermined range, such as a range comprising a mean amount of CAMP in felines that do not have any CKD.

Additionally or alternatively, some embodiments of the method diagnose the feline as not having early-stage CKD if the feline's measured amount of CAMP is equal to or less than a predetermined value, such as a mean amount of CAMP in felines that do not have any CKD, or is within a predetermined range, such as a range comprising a mean amount of CAMP in felines that do not have any CKD.

Additionally or alternatively, some embodiments of the method diagnose the feline as having early-stage CKD if the feline's measured amount of KIF12 exceeds a predetermined value, such as a mean amount of KIF12 in felines that do not have any CKD, or is outside of a predetermined range, such as a range comprising a mean amount of KIF12 in felines that do not have any CKD.

Additionally or alternatively, some embodiments of the method diagnose the feline as not having early-stage CKD if the feline's measured amount of KIF12 is equal to or less than a predetermined value, such as a mean amount of KIF12 in felines that do not have any CKD, or is within a predetermined range, such as a range comprising a mean amount of KIF12 in felines that do not have any CKD.

Additionally or alternatively, some embodiments of the method diagnose the feline as having early-stage CKD if the feline's measured amount of RBP4 exceeds a predetermined value, such as a mean amount of RBP4 in felines that do not have any CKD, or is outside of a predetermined range, such as a range comprising a mean amount of RBP4 in felines that do not have any CKD.

Additionally or alternatively, some embodiments of the method diagnose the feline as not having early-stage CKD if the feline's measured amount of RBP4 is equal to or less than a predetermined value, such as a mean amount of RBP4 in felines that do not have any CKD, or is within a predetermined range, such as a range comprising a mean amount of RBP4 in felines that do not have any CKD.

Additionally or alternatively, some embodiments of the method diagnose the feline as having early-stage CKD if the feline's measured amount of F10 exceeds a predetermined value, such as a mean amount of F10 in felines that do not have any CKD, or is outside of a predetermined range, such as a range comprising a mean amount of F10 in felines that do not have any CKD.

Additionally or alternatively, some embodiments of the method diagnose the feline as not having early-stage CKD if the feline's measured amount of F10 is equal to or less a corresponding predetermined value, such as a mean amount of F10 in felines that do not have any CKD, or is within a predetermined range, such as a range comprising a mean amount of F10 in felines that do not have any CKD.

Additionally or alternatively, some embodiments of the method diagnose the feline as having early-stage CKD if the feline's measured amount of ZKSCAN1 is less than a corresponding predetermined value, such as a mean amount of ZKSCAN1 in felines that do not have any CKD, or is outside of a range comprising a mean amount of ZKSCAN1 in felines that do not have any CKD.

Additionally or alternatively, some embodiments of the method diagnose the feline as not having early-stage CKD if the feline's measured amount of ZKSCAN1 is equal to or greater than a corresponding predetermined value, such as a mean amount of ZKSCAN1 in felines that do not have any CKD, or is within a predetermined range, such as a range comprising a mean amount of ZKSCAN1 in felines that do not have any CKD.

Additionally or alternatively, some embodiments of the method diagnose the feline as having early-stage CKD if the feline's measured amount of FN1 is less than a corresponding predetermined value, such as a mean amount of FN1 in felines that do not have any CKD, or is outside of a predetermined range, such as a range comprising a mean amount of FN1 in felines that do not have any CKD.

Additionally or alternatively, some embodiments of the method diagnose the feline as not having early-stage CKD if the feline's measured amount of FN1 is equal to or greater than a corresponding predetermined value, such as a mean amount of FN1 in felines that do not have any CKD, or is within a range comprising a mean amount of FN1 in felines that do not have any CKD.

In other preferred embodiments, which can be used in combination with one of more of the preferred embodiments disclosed above and/or without one or more of the preferred embodiments disclosed above, the predetermined value is a mean amount of the circulating protein in felines that have early-stage CKD, and/or the predetermined range is a range comprising a mean amount of the circulating protein in felines that have early-stage CKD. Preferably such a range comprises (i) a set of predetermined values less than the mean amount of the circulating protein in felines that have early-stage CKD, (ii) the mean amount of the circulating protein in felines that have early-stage CKD, and (iii) a set of predetermined values greater than the mean amount of the circulating protein in felines that have early-stage CKD.

For example, some embodiments of the method diagnose the feline as having early-stage CKD if the feline's measured amount of circulating ADIPOQ is equal to or greater than a predetermined value, such as a mean amount of circulating ADIPOQ in felines that have early-stage CKD, or is within a predetermined range, such as a range comprising a mean amount of circulating ADIPOQ in felines that have early-stage CKD.

Additionally or alternatively, some embodiments of the method diagnose the feline as not having early-stage CKD if the feline's measured amount of circulating ADIPOQ is less than a predetermined value, such as a mean amount of circulating ADIPOQ in felines that have early-stage CKD, or is outside of a predetermined range, such as a range comprising a mean amount of circulating ADIPOQ in felines that have early-stage CKD.

Additionally or alternatively, some embodiments of the method diagnose the feline as having early-stage CKD if the feline's measured amount of circulating CAMP is equal to or greater than a predetermined value, such as a mean amount of circulating CAMP in felines that have early-stage CKD, or is within a predetermined range, such as a range comprising a mean amount of circulating CAMP in felines that have early-stage CKD.

Additionally or alternatively, some embodiments of the method diagnose the feline as not having early-stage CKD if the feline's measured amount of circulating CAMP is less than a predetermined value, such as a mean amount of circulating CAMP in felines that have early-stage CKD, or is outside of a predetermined range, such as a range comprising a mean amount of circulating CAMP in felines that have early-stage CKD.

Additionally or alternatively, some embodiments of the method diagnose the feline as having early-stage CKD if the feline's measured amount of circulating KIF12 is equal to or greater than a predetermined value, such as a mean amount of circulating KIF12 in felines that have early-stage CKD, or is within a predetermined range, such as a range comprising a mean amount of circulating KIF12 in felines that have early-stage CKD.

Additionally or alternatively, some embodiments of the method diagnose the feline as not having early-stage CKD if the feline's measured amount of circulating KIF12 is less than a predetermined value, such as a mean amount of circulating KIF12 in felines that have early-stage CKD, or is outside of a predetermined range, such as a range comprising a mean amount of circulating KIF12 in felines that have early-stage CKD.

Additionally or alternatively, some embodiments of the method diagnose the feline as having early-stage CKD if the feline's measured amount of circulating RBP4 is equal to or greater than a predetermined value, such as a mean amount of circulating RBP4 in felines that have early-stage CKD, or is within a predetermined range, such as a range comprising a mean amount of circulating RBP4 in felines that have early-stage CKD.

Additionally or alternatively, some embodiments of the method diagnose the feline as not having early-stage CKD if the feline's measured amount of circulating RBP4 is less than a predetermined value, such as a mean amount of circulating RBP4 in felines that have early-stage CKD, or is outside of a predetermined range, such as a range comprising a mean amount of circulating RBP4 in felines that have early-stage CKD.

Additionally or alternatively, some embodiments of the method diagnose the feline as having early-stage CKD if the feline's measured amount of circulating F10 is equal to or greater than a predetermined value, such as a mean amount of circulating F10 in felines that have early-stage CKD, or is within a predetermined range, such as a range comprising a mean amount of circulating F10 in felines that have early-stage CKD.

Additionally or alternatively, some embodiments of the method diagnose the feline as not having early-stage CKD if the feline's measured amount of circulating F10 is less than a corresponding predetermined value, such as a mean amount of circulating F10 in felines that have early-stage CKD, or is outside of a predetermined range, such as a range comprising a mean amount of circulating F10 in felines that have early-stage CKD.

Additionally or alternatively, some embodiments of the method diagnose the feline as having early-stage CKD if the feline's measured amount of circulating ZKSCAN1 is equal to or less than a corresponding predetermined value, such as a mean amount of circulating ZKSCAN1 in felines that have early-stage CKD, or is within a range comprising a mean amount of circulating ZKSCAN1 in felines that have early-stage CKD.

Additionally or alternatively, some embodiments of the method diagnose the feline as not having early-stage CKD if the feline's measured amount of circulating ZKSCAN1 is greater than a corresponding predetermined value, such as a mean amount of circulating ZKSCAN1 in felines that have early-stage CKD, or is outside of a predetermined range, such as a range comprising a mean amount of circulating ZKSCAN1 in felines that have early-stage CKD.

Additionally or alternatively, some embodiments of the method diagnose the feline as having early-stage CKD if the feline's measured amount of circulating FN1 is equal to or less than a corresponding predetermined value, such as a mean amount of circulating FN1 in felines that have early-stage CKD, or is within a predetermined range, such as a range comprising a mean amount of circulating FN1 in felines that have early-stage CKD.

Additionally or alternatively, some embodiments of the method diagnose the feline as not having early-stage CKD if the feline's measured amount of circulating FN1 is greater than a corresponding predetermined value, such as a mean amount of circulating FN1 in felines that have early-stage CKD, or is outside of a range comprising a mean amount of circulating FN1 in felines that have early-stage CKD.

Some embodiments include the use of multiple markers to allow a diagnosis between early-stage and late-stage CKD. For example, the method can measure at least two of these circulating proteins, such as at least three, at least four, at least five, at least six, or even all seven of these circulating proteins, as biomarkers for early-stage CKD. When multiple markers are used, the diagnosis between early-stage CKD and late-stage CKD can be based on a simple majority if the markers indicate more than one stage of CKD, e.g., if seven markers are used and five of the seven indicate early-stage CKD and two of the seven indicate late-stage CKD, a diagnosis of early-stage CKD can be made.

Generally, a method of treating or slowing progression of chronic kidney disease in a feline can comprise any of the methods of diagnosing early-stage chronic kidney disease (CKD) in the feline disclosed herein; and the method can further comprise recommending, providing and/or administering a composition for the feline, wherein the composition treats or slows the progression of CKD in the feline, for example by administration to the feline in an amount effective to treat or slow the progression of CKD in the feline.

Such compositions can be any composition that is beneficial for providing nutrition to felines having CKD. In one embodiment, the composition can include a combination of glycine, methionine, cysteine, and glutamine. In one aspect, the amino acid blend of glycine, methionine, cysteine, and glutamine can be synergistic for treating renal cats. In another aspect, the amino acid blend can be free form amino acids. In still another aspect, the amino acid blend can further comprise at least one of protein, carbohydrates, fat, and fiber. In one embodiment, the composition can comprise medium chain triglycerides. In another embodiment, the composition can contain less than 1% of phosphorous compounds and/or phosphate compounds. In still another embodiment, the composition can contain less than 1% of potassium. In yet another embodiment, the composition can have protein and phosphorus in a ratio between 5:1 and 15:1. In one embodiment, the composition can comprise arginine, cicosapentaenoic acid, docosahexaenoic acid, vitamin E, and B vitamins. Such B vitamins can include any combination of vitamin B1 (thiamine), vitamin B2 (riboflavin), vitamin B3 (niacin, nicotinic acid, nicotinamide), vitamin B5 (pantothenic acid), vitamin B6 (pyridoxine, pyridoxal, pyridoxamine), vitamin B7 (biotin), vitamin B8 (myo-inositol), vitamin B9 (folic acid) vitamin B12 (cobalamin compounds including methylcobalamin, hydroxocobalamin, and cyanocobalamin). In another embodiment, the composition can comprise medium chain triglycerides (MCT), cicosapentaenoic acid (EPA), docosahexaenoic acid (DHA), arginine, antioxidants, and B vitamins. In one aspect, the antioxidants can include vitamin C and vitamin E.

Generally, the composition can be administered sufficiently such that the treatment is effective. In one aspect, the administration can be on a regular basis. In another aspect, the administration can be a long-term administration. Administration of the composition can include any manner of delivery. In one embodiment, the composition can be administered in conjunction with a pet food composition. In another embodiment, the composition is a pet food. In still another embodiment, the composition can be a sachet or supplement administered in conjunction with a pet food. In yet another embodiment, the composition can be a sachet or supplement administered separately from other food compositions.

Generally, the protein can be any crude protein material and may comprise vegetable proteins such as soybean meal, soy protein concentrate, corn gluten meal, wheat gluten, cottonseed, pea protein, canola meal, and peanut meal, or animal proteins such as casein, albumin, and meat protein. Examples of meat protein useful herein include beef, pork, lamb, equine, poultry, fish, and mixtures thereof. The compositions may also optionally comprise other materials such as whey and other dairy by-products. In one aspect, the protein comprises collagen, whey, or a mixture thereof. In one embodiment, the food compositions can comprise protein in amounts from about 10%, 20%, 30%, 35%, 40%, 45%, 50%, or even 55% to about 20%, 25%, 30%, 35%, 40%, 45%, 50%, 55%, 60%, or even 70% by weight, including various subranges within these amounts. In one aspect, the protein can be from about 20% to about 60% of the food composition by weight. In another aspect, the protein can be from about 25% to about 50% of the food composition by weight.

Additionally, the present compositions can comprise isoflavones. In various embodiments, the isoflavones include at least one of daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin. The isoflavones or metabolites thereof can be from soybean (*Glycine max*) in certain embodiments. Where present, the one or more metabolites preferably include equol. In one embodiment, the food compositions can comprise isoflavones in amounts from about 300, 400, 500, 600, 700, 800, 900, or even 1,000 mg per kg of the food composition to about 500; 600; 700; 800; 900; 1,000; 1,100; 1,200; 1,300; 1,400; or even 1,500 mg per kg of the food composition, including various subranges within these amounts. In one aspect, the isoflavones can present in an amount from about 300 mg to 1,500 mg per kilogram of the pet food composition. In another aspect, the isoflavones can present in an amount from about 700 mg to 1,200 mg per kilogram of the pet food composition.

Generally, any type of carbohydrate can be used in the food compositions. Examples of suitable carbohydrates include grains or cereals such as rice, corn, millet, sorghum, alfalfa, barley, soybeans, canola, oats, wheat, rye, triticale and mixtures thereof. In one embodiment, the carbohydrate comprises from about 10% to about 70% of the food composition by weight. In another embodiment, the carbohydrate comprises from about 20% to about 60% of the food compositions by weight. In other aspects, the carbohydrate can be present in amounts from about 10%, 20%, 30%, 40%, or even 50%, to about 20%, 30%, 40%, 50%, 60%, or even 70% by weight.

Generally, the food compositions include fat. Examples of suitable fats include animal fats and vegetable fats. In one aspect, the fat source can be an animal fat source such as tallow, lard, and/or poultry fat. Vegetable oils such as corn oil, sunflower oil, safflower oil, grape seed oil, soybean oil, olive oil, and/or coconut oils. Fish oil and other oils rich in monounsaturated and n-6 and n-3 polyunsaturated fatty acids, may also be used. In one embodiment, the food compositions can comprise fat in amounts from about 5%, 10%, 15%, 20%, 25%, 30%, 35%, 40%, 45%, or even 50% to about 15%, 20%, 25%, 30%, 35%, 40%, 45%, 50%, 55%, or even 60%, including various subranges within these amounts by weight. In one aspect, the fat comprises from about 10% to about 40% of the food composition by weight. In another aspect, the fat comprises from about 20% to about 35% of the food composition by weight.

In one embodiment, MCTs can be used and can be about 0.1 wt % to about 50 wt % of the composition. In other aspects, MCT can be present about 0.1 wt %, 1 wt %, or 3 wt % to about 5 wt %, 10 wt %, 15 wt %, or 20 wt % of the composition. In another embodiment, the composition can be administered in an amount that provides about 10 mg to 5 g of MCTs per kg body weight of the animal per day. In one aspect, 10 mg to about 500 mg of MCTs per kg body weight of the animal can be administered per day.

Additionally, the present compositions can comprise omega-3 fatty acids. Non-limiting examples of suitable omega-3 fatty acids include eicosapentaenoic acid (EPA), docosahexaenoic acid (DHA), alpha-linolenic acid (ALA) and mixtures thereof. In one embodiment, the omega-3 fatty acids can range from about 0.2%, 0.5%, 1%, 2%, or even 3% to about 1%, 2%, 3%, 4%, or even 5% of the composition by weight. In some embodiments, the omega-3 fatty acids are present in the food composition in an amount from about 1% to about 5% by weight. In some embodiments, the omega-3 fatty acids are present in the food composition in an amount from about 1% to about 2% by weight.

In addition to the fats and fatty acids discussed herein, the present compositions can comprise omega-6 fatty acids. Non-limiting examples of suitable omega-6 fatty acids include linoleic acid (LA), gamma-linolenic acid (GLA), arachidonic acid (AA, ARA), cicosadienoic acid, docosadienoic acid, and mixtures thereof. In one embodiment, the omega-6 fatty acids can range from about 0.2%, 0.5%, 1%, 2%, or even 3% to about 1%, 2%, 3%, 4%, or even 5% of the composition by weight. In some embodiments, the omega-6 fatty acids are present in the food composition in an amount from about 1% to about 5% by weight. In some embodiments, the omega-6 fatty acids are present in the food composition in an amount from about 1% to about 2% by weight.

The administration of the pet food compositions can be performed on as-needed basis, an as-desired basis, a regular basis, or intermittent basis. In one aspect, the food composition can be administered to the animal on a regular basis. In one aspect, at least weekly administration can be performed. More frequent administration or consumption, such as twice or three times weekly, can be performed in certain embodiments. In one aspect, an administration regimen can comprise at least once daily consumption.

Preferably, administration in the methods disclosed herein, including administration as part of a dietary regimen, can span a period ranging from parturition through the adult life of the animal. In certain embodiments, the animal can be a young or growing animal. In other embodiments, administration can begin, for example, on a regular or extended regular basis, when the animal has reached more than about 10%, 20%, 30%, 40%, or 50% of its projected or anticipated lifespan. In some embodiments, the animal can have attained 40, 45, or 50% of its anticipated lifespan. In yet other embodiments, the animal can be older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

Such administration can be performed for a time required to accomplish one or more objectives described herein, e.g., treating renal disease. Other administration amounts may be appropriate and can be determined based on the animal's initial weight as well as other variables such as species, gender, breed, age, desired health benefit, etc.

The moisture content for pet food compositions varies depending on the nature of the food composition. The food compositions may be dry compositions (e.g., kibble), semi-moist compositions, wet compositions, or any mixture thereof. In one embodiment, the composition can be a complete and nutritionally balanced pet food. In this embodiment, the pet food may be a "wet food", "dry food", or food of "intermediate moisture" content. "Wet food" describes pet food that is typically sold in cans or foil bags and has a moisture content typically in the range of about 70% to about 90%. "Dry food" describes pet food that is of a similar composition to wet food but contains a limited moisture content typically in the range of about 5% to about 15% or 20% (typically in the form or small biscuit-like kibbles). In one embodiment, the compositions can have moisture content from about 5% to about 20%. Dry food products include a variety of foods of various moisture contents, such that they are relatively shelf-stable and resistant to microbial or fungal deterioration or contamination. Also, in one aspect, dry food compositions can be extruded food products for companion animals.

The food compositions may also comprise one or more fiber sources. Such fiber sources include fiber that is soluble, insoluble, fermentable, and nonfermentable. Such fibers can be from plant sources such as marine plants, but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, corn bran, wheat bran, oat bran, carob bean gum, citrus pulp, pectin, fructooligosaccharide, short chain oligofructose, mannanoligofructose, soy fiber, arabinogalactan, galactooligosaccharide, arabinoxylan, cellulose, chicory, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefits described herein or to the immune system of an animal.

In one embodiment, the food compositions can include a total dietary fiber from about 1% to about 15% by weight. In some aspects, the total dietary fiber can be included in an amount from about 5% to about 15% by weight, or even from about 8% to about 13% by weight. In another embodiment, the food compositions can include crude fiber from about 1% to about 10% by weight. In some aspects, the crude fiber can be included in an amount from about 3% to about 10% by weight, or even from about 3% to about 7% by weight.

In some embodiments, the ash content of the food composition ranges from less than 1% to about 15%. In one aspect, the ash content can be from about 5% to about 10%.

Generally, the food composition can be a meal, component of a meal, a snack, supplement, or a treat. Such compositions can include complete foods intended to supply the necessary dietary requirements for an animal.

Pet food compositions may further comprise one or more substances such as vitamins, minerals, antioxidants, probiotics, prebiotics, salts, and functional additives such as palatants, colorants, emulsifiers, and antimicrobial or other preservatives. Non-limiting examples of suitable preservatives include potassium sorbate, sorbic acid, sodium methyl para-hydroxybenzoate, calcium propionate, propionic acid, and combinations thereof. Minerals that may be useful in such compositions include, for example, calcium, phosphorous, potassium, sodium, iron, chloride, boron, copper, zinc, magnesium, manganese, iodine, selenium, and the like. Examples of additional vitamins useful herein include such fat-soluble vitamins as A, D, E, and K and water-soluble vitamins including B vitamins, and vitamin C. Inulin, amino acids, enzymes, coenzymes, and the like may be useful to include in various embodiments.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

For example, the amount of any of the above-noted ingredients can be decreased or increased based on the estimated effect on CKD in a feline.

In view of the above, an aspect of the present disclosure is a method of diagnosing CKD in a feline, the method comprising:

- measuring an amount of each of at least one circulating protein from the feline, wherein the at least one circulating protein is selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof;
- performing comparison of the amount of each of the at least one circulating protein from the feline to a corresponding predetermined value or a corresponding predetermined range; and
- diagnosing the feline as having early-stage CKD or not having early-stage CKD, based on the comparison.

The method may comprise obtaining a sample of at least one of serum or plasma from the feline, wherein the measuring of the amount of each of the at least one circulating protein is performed on the sample of at least one of serum or plasma. The measuring and the comparison may use at least two of the circulating proteins selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof. The feline may be a senior cat.

Another aspect of the present disclosure is a method of treating or slowing progression of CKD in a feline, the method comprising diagnosing CKD in the feline according to any embodiment as disclosed herein and further comprising recommending a composition for the feline, wherein the composition is formulated to treat or slow the progression of CKD in the feline.

Yet another aspect of the present disclosure is a method of treating or slowing progression of CKD in a feline, the method comprising any method of diagnosing CKD in the feline as disclosed herein and further comprising providing a composition for the feline, wherein the composition is formulated to treat or slow the progression of CKD in the feline In these methods, the composition may be a pet food composition or administered in conjunction with a pet food composition. The composition may include one or more of (i) a combination of glycine, methionine, cysteine, and glutamine; (ii) medium chain triglycerides; (iii) a combination of arginine, eicosapentaenoic acid, docosahexaenoic acid, vitamin E, and B vitamins; or (iv) protein and phosphorus in a ratio between 5:1 and 15:1. The composition may contain less than 1% of potassium and contain less than 1% of phosphorous compounds and phosphate compounds.

The method may further comprise administering the composition to the feline in an amount effective to treat or slow the progression of CKD in the feline.

EXAMPLES

The following non-limiting examples are illustrative of embodiments of the present disclosure.

Example 1-CKD Study of Felines

CKD diagnosis and staging were performed according to the current IRIS guidelines (http://www.iris-kidney.com/guidelines/index.html). Serum samples were collected from 25 non-CKD cats (also called control) and 16 cats with early (IRIS stages 1 and 2, also called early CKD) and 7 cats with late (IRIS stages 3 and 4, also called late CKD) stages of CKD. The hypothesis was that altered levels of serum proteins may reflect CKD stages in cats. One or a panel of these protein markers may be used to diagnose CKD. To assess cat serum, proteomic techniques, previously developed and applied to human blood samples, were translated to feline samples.

Methods for Proteomics Analysis:

Materials.

Most chemicals were purchased from Sigma (St. Louis, MO). $H_2O$ was obtained from a Milli-Q apparatus (Merck Millipore, Billerica, MA). The 6-plex tandem mass tag (TMT) isobaric label kits were purchased from Thermo Scientific (Rockford, IL). Sequencing-grade modified trypsin/Lys-C was from Promega (Madison, WI). Oasis HLB cartridges (1 $cm^3$, 30 mg) were acquired from Waters (Milford, MA). Strata-X-C 33u Polymeric strong cation-exchange (SCX) cartridges (30 mg/1 mL) were from Phenomenex (Torrance, CA).

Sample Preparation

To a volume of 1.2 μL of each cat serum sample was added 5 μL of sodium dodecyl sulfate 2% in $H_2O$ containing β-lactoglobulin (LACB) from bovine milk at 0.12 μg/μL. Samples were diluted in 95 μL of triethylammonium hydrogen carbonate buffer (TEAB) 100 mM, reduced with 5.3 μL of tris (2-carboxyethyl) phosphine hydrochloride 20 mM in $H_2O$, alkylated with 5.5 μL of iodoacetamide 150 mM in $CH_3CN$, digested with 10 μL trypsin/Lys-C at 0.25 μg/μL in TEAB 100 mM, and 6-plex TMT labeled (addition of 41 μL of reagent at 18.5 μg/μL in $CH_3CN$). After reaction quenching with hydroxylamine 5% in $H_2O$, sets of six differentially labeled samples were pooled. Solid-phase extraction purifications (Oasis HLB and SCX) were performed. These procedures were previously described and performed using a 4-channels Microlab Star liquid handler (Hamilton, Bonaduz, Switzerland).

Reversed-Phase Liquid Chromatography Tandem Mass Spectrometry (RP-LC MS/MS).

The dried samples were dissolved in 1000 μL $H_2O/CH_3CN$/formic acid (FA) 96.9/3/0.1. RP-LC MS/MS was performed with an Ultimate 3000 RSLC nano system and an Orbitrap Fusion Lumos Tribrid mass spectrometer (Thermo Scientific). Peptides (injection of 2.5 μL) were trapped on an Acclaim PepMap 300 μm×5 mm (C18, 5 μm, 100 Å) pre-column, and separated on an Acclaim PepMap RSLC 75 μm×50 cm (C18, 2 μm, 100 Å) column (Thermo Scientific) coupled to a stainless steel nanobore emitter (40 mm, OD 1/32") (Thermo Scientific). The column was heated to 50° C. using a PRSO-V1 column oven (Sonation, Biberach, Germany). Peptide separation was performed with a gradient of mobile phase A ($H_2O/CH_3CN/FA$ 97.9/2/0.1) and B ($H_2O/CH_3CN/FA$ 19.92/80/0.08): from 6.3% (hold for 1 min) to 11% B over 11 min, from 11% to 17.5% B over 75 min, from 17.5% to 25.5% B over 42 min and from 25.5% to 40% B over 28 min, with final elution (98% B) and equilibration (6.3% B) for a further 23 min. The flow rate was 300 nL/min.

Data were acquired using a data-dependent method. A positive ion spray voltage of 1900 V and a transfer tube temperature of 275° C. were set up. For MS survey scans in profile mode, the Orbitrap resolution was 120000 (automatic gain control (AGC) target of $2\times 10^5$) with a m/z scan range from 300 to 1500, RF lens set at 30%, and a maximum injection time of 100 ms. For MS/MS with higher-energy collisional dissociation at 35% of the normalized collision energy, AGC target was set to $1\times10^5$ (isolation width of 0.7 in the quadrupole), with a resolution of 30000, first mass at m/z=100, and a maximum injection time of 105 ms with Orbitrap acquiring in profile mode. A maximum duty cycle time of 3 s was used. Dynamic exclusion was set for 60 s and a ±10 ppm window. A lock mass of m/z=445.12002 was used.

Data Processing and Analysis.

Identification was performed against the cat UniProtKB database (*Felis catus, November* 2020 release) including the LACB sequence (40213 entries in total). Mascot (version 2.6.1, Matrix Sciences, London, UK) was used as the search engine using ProteoWizard msConvert 3.0 for data import. Variable amino acid modifications were oxidized methionine, deamidated asparagine/glutamine, and 6-plex TMT-labeled peptide amino terminus; 6-plex TMT-labeled lysine was set as fixed modification as well as carbamidomethylation of cysteine. Trypsin was selected as the proteolytic enzyme, with a maximum of two potential missed cleavages. Peptide and fragment ion tolerances were set to 10 ppm and 0.02 Da, respectively.

Mascot results files were loaded into Scaffold Q+5.0.0 (Proteome Software, Portland, OR) to be further searched with X! Tandem (The GPM, thegpm.org; version Alanine (2017.2.1.4)). Both peptide and protein false discover rates were fixed at 1% maximum, with a two-unique-peptide criterion to report protein identification. TMT quantitative values were exported as logarithm to the base 2 of the protein ratio fold change, with normalization applied between samples and experiments.

Statistical Analysis

Statistical analyses were conducted on R Studio. One-way analysis of variance (ANOVA) were used for each protein (values corrected by sex via linear regression models) to determine the significance of difference between the means of the 3 groups of cats (i.e., Controls, Early CKD and Late CKD) with post Tukey multiple comparisons of the means for pair-wise comparison of groups. Missing values were imputed using the K-nearest neighbors method. Log-transformed protein values were standardized so that the mean is equal to 0 and standard deviation is equal to 1.

TABLE 1

| | | | Means | | |
|---|---|---|---|---|---|
| Proteins | Symbols | p-value | Control | Early CKD | Late CKD |
| Adiponectin, C1Q and collagen domain containing | ADIPOQ | 5.32E−03 | −0.072 | 0.189 | −0.175 |
| Cathelicidin | CAMP | 9.84E−04 | −0.172 | 0.108 | 0.366 |
| Kinesin-like protein | KIF12 | 6.53E−06 | −0.065 | 0.012 | 0.203 |
| Plasma retinol-binding protein | RBP4 | 3.36E−05 | −0.103 | 0.025 | 0.31 |
| Ig-like domain-containing protein | ZKSCAN1 | 2.45E−03 | 0.075 | −0.041 | −0.172 |
| Coagulation factor X | F10 | 3.69E−04 | −0.053 | 0.017 | 0.152 |
| Fibronectin | FN1 | 1.24E−03 | 0.085 | −0.032 | −0.229 |

Seven feline circulating proteins were identified as markers for early-stage CKD in cats (Table 1), specifically, adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), and fibronectin (FN1). Urinary ADIPOQ has previously been shown to be a potential diagnostic marker for feline CKD. Urinary RBP4 as a putative renal marker in the cats has also been reported. In addition, glomerular FN1 was previously shown to increase in cats with tubulointerstitial nephritis, but to the contrary, the experimental data disclosed herein showed that serum level of FN1 was decreased in cat with early CKD. These seven serum proteins can be used alone or in combination as diagnostic markers in cats with early-stage CKD. Based on the present means data, calculated ranges for diagnosis are presented in Table 2.

TABLE 2

| | | Means | | |
|---|---|---|---|---|
| Proteins | Symbols | No CKD | Early CKD* | Late CKD |
| Adiponectin, C1Q and collagen domain containing | ADIPOQ | <0.059 | ≥0.059 | N/A |
| Cathelicidin | CAMP | <−0.032 | [−0.032, 0.237] | >0.237 |
| Kinesin-like protein | KIF12 | <−0.027 | [−0.027, 0.1075] | >0.1075 |
| Plasma retinol-binding protein | RBP4 | <−0.039 | [−0.039, 0.1675] | >0.1675 |

TABLE 2-continued

| | | Means | | |
|---|---|---|---|---|
| Proteins | Symbols | No CKD | Early CKD* | Late CKD |
| Ig-like domain-containing protein | ZKSCAN1 | >0.017 | [−0.1065, 0.017] | <−0.1065 |
| Coagulation factor X | F10 | <−0.018 | [−0.018, 0.0845] | >0.0845 |
| Fibronectin | FN1 | >0.027 | [−0.1305, 0.027] | <−0.1305 |

*Diagnosis of early CKD includes any value between the bracketed numbers including endpoints As shown in Table 2, a method of diagnosing non-CKD cats, early-stage CKD cats, and late-stage CKD cats can include measuring a protein selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof; and determining that the cat is non-CKD if the value of the measured protein is under the "No CKD" column, determining the cat is early-stage CKD if the value of the measured protein is under the "Early CKD*" column, or determining the cat is late-stage CKD if the value of the measured protein if under the "Late CKD" column. As discussed herein, multiple markers can be used. If more than one marker is used and not all markers correspond to the same diagnosis, a majority of markers that correspond to the same diagnosis can be used as the basis of the diagnosis. For example, if ADIPOQ, CAMP, and KIF12 are used and two correspond to Early CKD and one corresponds to No CKD, the cat can be diagnosed as early-stage CKD.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of diagnosing chronic kidney disease (CKD) in a feline, the method comprising:
- measuring an amount of each of at least two circulating proteins from the feline, wherein the at least two circulating proteins are selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof;
- performing comparison of the amount of each of the at least two circulating proteins from the feline to a corresponding predetermined value or a corresponding predetermined range; and
- diagnosing the feline as having early-stage CKD or not having early-stage CKD, based on the comparison.

2. The method of claim 1, comprising obtaining a sample of at least one of serum or plasma from the feline, wherein the measuring of the amount of each of the at least two circulating proteins is performed on the sample of at least one of serum or plasma.

3. The method of claim 1, wherein the feline is a senior cat.

4. A method of treating or slowing progression of chronic kidney disease (CKD) in a feline, the method comprising diagnosing CKD in the feline according to claim 1 and further comprising providing a composition for the feline, wherein the composition is formulated to treat or slow the progression of CKD in the feline.

5. The method of claim 4 wherein the composition includes a combination of glycine, methionine, cysteine, and glutamine.

6. The method of claim 4, wherein the composition comprises medium chain triglycerides.

7. The method of claim 4, wherein the composition comprises arginine, eicosapentaenoic acid, docosahexaenoic acid, vitamin E, and B vitamins.

8. The method of claim 4, wherein the composition contains less than 1% of potassium and contains less than 1% of phosphorous compounds and phosphate compounds.

9. The method of claim 4, wherein the composition has protein and phosphorus in a ratio between 5:1 and 15:1.

10. The method of claim 4, wherein the composition is a pet food composition or is administered in conjunction with a pet food composition.

11. A method of treating or slowing progression of chronic kidney disease (CKD) in a feline, the method comprising diagnosing CKD in the feline according to claim 1 and further comprising administering a composition to the feline in an amount effective to treat or slow the progression of CKD in the feline.

12. The method of claim 11, wherein the composition includes a combination of glycine, methionine, cysteine, and glutamine.

13. The method of claim 11, wherein the composition comprises medium chain triglycerides.

14. The method of claim 11, wherein the composition comprises arginine, eicosapentaenoic acid, docosahexaenoic acid, vitamin E, and B vitamins.

15. The method of claim 11, wherein the composition contains less than 1% of potassium and contains less than 1% of phosphorous compounds and phosphate compounds.

16. The method of claim 11, wherein the composition has protein and phosphorus in a ratio between 5:1 and 15:1.

17. The method of claim 11, wherein the composition is a pet food composition or is administered in conjunction with a pet food composition.

18. The method of claim 1, wherein the at least two circulating proteins, which are measured and compared to the corresponding predetermined value or corresponding predetermined range, comprise at least three of the circulating proteins selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof.

19. The method of claim 4, wherein the at least two circulating proteins, which are measured and compared to the corresponding predetermined value or corresponding predetermined range, comprise at least three of the circulating proteins selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof.

20. The method of claim 11, wherein the at least two circulating proteins, which are measured and compared to the corresponding predetermined value or corresponding predetermined range, comprise at least three of the circulating proteins selected from the group consisting of adiponectin (ADIPOQ), cathelicidin (CAMP), kinesin-like protein (KIF12), plasma retinol-binding protein (RBP4), Ig-like domain-containing protein (ZKSCAN1), coagulation factor X (F10), fibronectin (FN1) and mixtures thereof.

* * * * *